(12) United States Patent
Braje et al.

(10) Patent No.: US 8,492,540 B2
(45) Date of Patent: Jul. 23, 2013

(54) 1,2,4,-TRIAZIN-3,5-DIONE COMPOUNDS SUITABLE FOR TREATING DISORDERS THAT RESPOND TO MODULATION OF THE DOPAMINE $D_3$ RECEPTOR

(75) Inventors: Wilfried Braje, Ludwigshafen (DE); Sean Colm Turner, Ludwigshafen (DE); Andreas Haupt, Ludwigshafen (DE); Udo Lange, Ludwigshafen (DE); Hervé Geneste, Ludwigshafen (DE); Karla Drescher, Ludwigshafen (DE); Liliane Unger, Ludwigshafen (DE); Ana Lucia Relo, Ludwigshafen (DE); Anton Bespalov, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 55 days.

(21) Appl. No.: 12/740,714

(22) PCT Filed: Oct. 31, 2008

(86) PCT No.: PCT/EP2008/064795
§ 371 (c)(1),
(2), (4) Date: Aug. 25, 2010

(87) PCT Pub. No.: WO2009/056625
PCT Pub. Date: May 7, 2009

(65) Prior Publication Data
US 2010/0311755 A1    Dec. 9, 2010

(30) Foreign Application Priority Data
Nov. 2, 2007  (EP) .................................... 07119927

(51) Int. Cl.
*C07D 253/075*  (2006.01)
*C07D 403/14*  (2006.01)
*A61K 31/53*  (2006.01)
*A61P 25/18*  (2006.01)
*A61P 25/30*  (2006.01)
*A61P 25/00*  (2006.01)

(52) U.S. Cl.
USPC ......................................... 544/182; 514/242

(58) Field of Classification Search
USPC .......................................... 544/182; 514/242
See application file for complete search history.

(56) References Cited

U.S. PATENT DOCUMENTS

| | | | |
|---|---|---|---|
| 5,977,106 A | 11/1999 | Patoiseau et al. | |
| 6,090,807 A | 7/2000 | Hellendahl et al. | |
| 6,124,294 A | 9/2000 | Hellendahl et al. | |
| 6,191,130 B1 * | 2/2001 | Patoiseau et al. | 514/242 |
| 6,342,604 B1 | 1/2002 | Hellendahl et al. | |
| 6,472,392 B1 | 10/2002 | Starck et al. | |
| 2006/0235004 A1 | 10/2006 | Geneste et al. | |
| 2008/0161322 A1 | 7/2008 | Geneste et al. | |
| 2008/0261992 A1 | 10/2008 | Geneste et al. | |
| 2009/0054449 A1 | 2/2009 | Geneste et al. | |

FOREIGN PATENT DOCUMENTS

| | | |
|---|---|---|
| EP | 1484330 A1 | 8/2004 |
| WO | 9602246 | 2/1996 |
| WO | 9602519 | 2/1996 |
| WO | 9602520 | 2/1996 |
| WO | 9616949 | 6/1996 |
| WO | 9902503 | 1/1999 |
| WO | 2004/080981 A1 | 3/2004 |
| WO | 2004080981 | 9/2004 |
| WO | 2004108706 | 12/2004 |
| WO | 2005118558 | 12/2005 |

(Continued)

OTHER PUBLICATIONS

Le Foil et al., PubMed Abstract (Expert Opinion Investig Drugs, 16(1):45-57), Jan. 2007.*
Sokoloff, P., et al., Arzneim. Forsch./Drug Res. 42(1), p. 224 (1992).
Dooley, M., et al., Drugs and Aging (1998), 12, pp. 495-514.
Joyce, J.N., Pharmacology and Therapeutics (2001), 90, pp. 231-259.
Schwartz, J.C., et al., The dopamine D3 receptor as a target for antipsychotics, 1992, pp. 135-144.

(Continued)

*Primary Examiner* — Venkataraman Balasubramanian
(74) *Attorney, Agent, or Firm* — Lisa V. Mueller; Michael Best & Friedrich LLP

(57) ABSTRACT

The invention relates to compounds of the formula I:

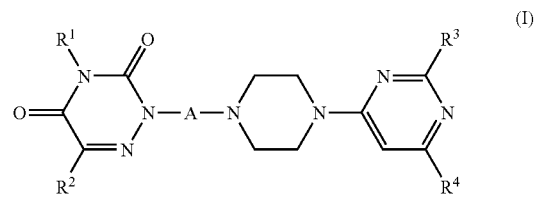

wherein
A is a saturated or unsaturated hydrocarbon chain having a chain length of 4 to 6 carbon atoms, the hydrocarbon chain being unsubstituted or substituted by 1, 2 or 3 methyl groups;
$R^1$ is selected from the group consisting of hydrogen, $C_1$-$C_3$ alkyl and fluorinated $C_1$-$C_3$ alkyl;
$R^2$ is hydrogen, halogen, cyano, $C_1$-$C_3$ alkyl, $C_1$-$C_3$ alkoxy, fluorinated $C_1$-$C_3$ alkyl or fluorinated $C_1$-$C_3$ alkoxy;
$R^3$ is selected from the group consisting of branched $C_4$-$C_6$ alkyl and $C_3$-$C_6$ cycloalkyl, and
$R^4$ is $C_1$-$C_6$ alkyl, $C_3$-$C_6$ cycloalkyl, fluorinated $C_1$-$C_3$-alkyl and fluorinated $C_3$-$C_6$ cycloalkyl.
and the physiologically tolerated salts of these compounds and the N-oxides thereof.
The invention also relates to a pharmaceutical composition that comprises at least one compound of the formula I and/or at least one physiologically tolerated acid addition salt thereof, and further to a method for treating disorders that respond beneficially to dopamine $D_3$ receptor antagonists or dopamine $D_3$ agonists, said method comprising administering an effective amount of at least one compound or physiologically tolerated acid addition salt of the formula I to a subject in need thereof.

20 Claims, No Drawings

FOREIGN PATENT DOCUMENTS

| | | |
|---|---|---|
| WO | 2005118571 | 12/2005 |
| WO | 2006015842 | 2/2006 |
| WO | 2006/058753 A1 | 6/2006 |
| WO | 2006/066885 A1 | 6/2006 |

OTHER PUBLICATIONS

Sokoloff, P., et al., Nature, 347, p. 146 (1990).

International Search Report issued in PCT/EP08/064795 dated Jan. 23, 2009.

Opposition Brief received Sep. 22, 2010 and filed by the Dominican Association of Pharmaceutical Industries against corresponding DO Patent Application P2010-0126.

* cited by examiner

1,2,4,-TRIAZIN-3,5-DIONE COMPOUNDS SUITABLE FOR TREATING DISORDERS THAT RESPOND TO MODULATION OF THE DOPAMINE $D_3$ RECEPTOR

CROSS-REFERENCE TO RELATED APPLICATIONS

This is the U.S. national stage entry of International Patent Application No. PCT/EP2008/064795, filed on Oct. 31, 2008, which claims priority to European Patent Application No. EP 07119927.7, filed Nov. 2, 2007, the contents of all of which are hereby incorporated by reference.

BACKGROUND OF THE INVENTION

The present invention relates to novel 1,2,4-triazin-3,5-dione compounds, in particular to the compounds of the formula I as described herein. The compounds possess valuable therapeutic properties and are suitable, in particular, for treating diseases that respond to modulation of the dopamine $D_3$ receptor.

Neurons obtain their information by way of G protein-coupled receptors, inter alia. A large number of substances exert their effect by way of these receptors. One of them is dopamine. Confirmed findings exist with regard to the presence of dopamine and its physiological function as a neurotransmitter. Disorders in the dopaminergic transmitter system result in diseases of the central nervous system which include, for example, schizophrenia, depression and Parkinson's disease. These diseases, and others, are treated with drugs which interact with the dopamine receptors.

Up until 1990, two subtypes of dopamine receptor had been clearly defined pharmacologically, termed $D_1$ and $D_2$ receptors. More recently, a third subtype was found, namely, the $D_3$ receptor which appears to mediate some effects of antipsychotics and antiparkinsonian drugs (J. C. Schwartz et al., "The Dopamine $D_3$ Receptor as a Target for Antipsychotics" in Novel Antipsychotic Drugs, H. Y. Meltzer, ed., Raven Press, New York 1992, pages 135-144; M. Dooley et al., Drugs and Aging 1998, 12:495-514; J. N. Joyce, Pharmacology and Therapeutics 2001, 90:231-59, "The Dopamine $D_3$ Receptor as a Therapeutic Target for Antipsychotic and Antiparkinsonian Drugs"). Since then, the dopamine receptors have been divided into two families. On the one hand, there is the $D_2$ group, consisting of $D_2$, $D_3$ and $D_4$ receptors, and, on the other hand, the $D_1$ group, consisting of $D_1$ and $D_5$ receptors.

Whereas $D_1$ and $D_2$ receptors are widely distributed, $D_3$ receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression, $D_3$ receptors are regarded as being a target having few side-effects and it is assumed that while a selective $D_3$ ligand would have the properties of known antipsychotics, it would not have their dopamine $D_2$ receptor-mediated neurological side-effects (P. Sokoloff et al., Arzneim. Forsch./Drug Res. 42(1):224 (1992), "Localization and Function of the $D_3$ Dopamine Receptor"; P. Sokoloff et al., Nature, 347:146 (1990), "Molecular Cloning and Characterization of a Novel Dopamine Receptor ($D_3$) as a Target for Neuroleptics").

Heterocyclic compounds having an affinity for the dopamine $D_3$ receptor have been described previously on various occasions, as for example in WO 96/02246, WO 96/02519, WO 96/02520, WO 99/02503, WO 2004/080981, WO2004/108706, WO 2005/118558, WO 2005/118571 and WO 2006/015842. These compounds possess high affinities for the dopamine $D_3$ receptor, and have therefore been proposed as being suitable for treating diseases of the central nervous system. Unfortunately, their selectivity towards the $D_3$ receptor is not always satisfactory. Moreover, some of these compounds have an unfavorable DMPK profile (DMPK: metabolic stability and pharmacokinetics), in particular in terms of microsomal stability and in vivo half-life or a poor bioavailability. Consequently there is an ongoing need to provide new compounds, which have an improved selectivity towards $D_3$ receptors or an improved pharmacological profile, such as a favorable DMPK profile, and/or a high bioavailability.

U.S. Pat. No. 5,977,106 describes 1,2,4-triazin-3,5-dione compounds which are ligands towards the serotoninergic 5HT1 receptor.

SUMMARY OF THE INVENTION

It has now been found that certain 1,2,4-triazin-3,5-dione compounds exhibit, to a surprising and unexpected degree, highly selective binding to the dopamine $D_3$ receptor as well as a favorable DMPK profile, in particular in terms of metabolic stability (determined e.g. by microsomal stability and/or in vivo half-life). Such compounds are those having the general formula I, their pharmaceutically tolerable salts, to the tautomers and to the N-oxides thereof:

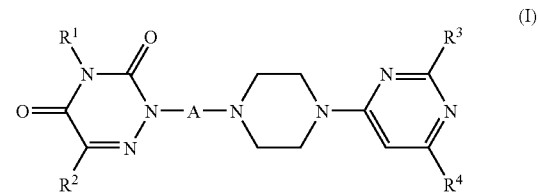

wherein
A is a saturated or unsaturated hydrocarbon chain having a chain length of 4 to 6 carbon atoms, the hydrocarbon chain being unsubstituted or substituted by 1, 2 or 3 methyl groups;
$R^1$ is selected from the group consisting of hydrogen, $C_1$-$C_3$ alkyl and fluorinated $C_1$-$C_3$ alkyl;
$R^2$ is hydrogen, halogen, cyano, $C_1$-$C_3$ alkyl, $C_1$-$C_3$ alkoxy, fluorinated $C_1$-$C_3$ alkyl or fluorinated $C_1$-$C_3$ alkoxy;
$R^3$ is selected from the group consisting of branched $C_4$-$C_6$ alkyl and $C_3$-$C_6$ cycloalkyl, and
$R^4$ is $C_1$-$C_6$ alkyl, $C_3$-$C_6$ cycloalkyl, fluorinated $C_1$-$C_3$ alkyl and fluorinated $C_3$-$C_6$ cycloalkyl.

The present invention therefore relates to 1,2,4-triazin-3, 5-dione compounds of the general formula I, as well as to their physiologically tolerated salts, to the tautomers of I and to the physiologically tolerated salts, to the N-oxides of the compounds I and to their physiologically tolerated salts.

The present invention also relates to a pharmaceutical composition which comprises at least one active compound selected from 1,2,4-triazin-3,5-dione compounds of the formula I, their physiologically tolerated salts, the tautomers of I, the physiologically tolerated salts of the compounds of formula I, and the N-oxides thereof, where appropriate together with physiologically acceptable carriers and/or auxiliary substances.

The present invention also relates to a method for treating disorders which respond to influencing by dopamine $D_3$ receptor antagonists or dopamine $D_3$ agonists, said method comprising administering an effective amount of at least one active compound selected from 1,2,4-triazin-3,5-dione compounds of the formula I, their physiologically tolerated salts, the tautomers of I, the physiologically tolerated salts of the compounds of formula I, and the N-oxides thereof, to a subject in need thereof.

DETAILED DESCRIPTION OF THE INVENTION

The diseases which respond to the influence of dopamine $D_3$ receptor antagonists or agonists include disorders and diseases of the central nervous system, in particular affective disturbances, neurotic disturbances, stress disturbances and somatoform disturbances and psychoses, and especially schizophrenia, depression, bipolar disorder, substance abuse (also termed drug abuse), dementia, major depressive disorder, anxiety, autism, attention deficit disorder with or without hyperactivity and personality disorder. In addition, $D_3$-mediated diseases may include disturbances of kidney function, in particular kidney function disturbances which are caused by diabetes such as diabetes mellitus, also termed as diabetic nephropathy (see WO 00/67847).

According to the invention, one or more compounds of the general formula I having the meanings mentioned at the outset can be used for treating the above-mentioned indications. Provided the compounds of the formula I possess one or more centers of asymmetry, it is also possible to use enantiomeric mixtures, in particular racemates, diastereomeric mixtures and tautomeric mixtures; preferred, however, are the respective essentially pure enantiomers, diastereomers and tautomers.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, nitric acid, sulfuric acid, organic sulfonic acids having from 1 to 12 carbon atoms, e.g. $C_1$-$C_4$-alkylsulfonic acids such as methanesulfonic acid, cycloaliphatic sulfonic acids such as S-(+)-10-camphorsulfonic acids and aromatic sulfonic acids such as benzenesulfonic acid and toluenesulfonic acid, di- and tricarboxylic acids and hydroxycarboxylic acids having from 2 to 10 carbon atoms such as oxalic acid, malonic acid, maleic acid, fumaric acid, mucic acid, lactic acid, tartaric acid, citric acid, glycolic acid and adipic acid, as well as cis- and trans-cinnamic acid, furoic acid and benzoic acid. Other utilizable acids are described in Fortschritte der Arzneimittelforschung [Advances in Drug Research], Volume 10, pages 224 ff., Birkhäuser Verlag, Basel and Stuttgart, 1966. The physiologically tolerated salts of compounds of the formula I may be present as the mono-, bis-, tris- and tetrakis-salts, that is, they may contain 1, 2, 3 or 4 of the aforementioned acid molecules per molecule of formula I. The acid molecules may be present in their acidic form or as an anion.

As used herein, $C_1$-$C_3$ alkyl is a straight-chain or branched alkyl group having 1, 2 or 3 carbon atoms. Examples of such a group are methyl, ethyl, n-propyl and isopropyl.

As used herein, $C_1$-$C_6$ alkyl is a straight-chain or branched alkyl group having 1 to 6 carbon atoms. Examples of such a group are methyl, ethyl, n-propyl, isopropyl, n-butyl, 2-butyl, isobutyl, tert. butyl (1,1-dimethylethyl), n-pentyl, 2-pentyl, 2-methylbutyl, 3-methylbutyl, 1,1-dimethylpropyl, 1,2-dimethylpropyl, n-hexyl, 2-hexyl, 2-methylpentyl etc.

As used herein, fluorinated $C_1$-$C_3$ alkyl is a straight-chain or branched alkyl group having 1, 2 or 3 carbon atoms, wherein at least one, e.g. 1, 2, 3, 4 or 5 hydrogen atoms or all hydrogen atoms are replaced by fluorine atoms. Examples of such a group are fluoromethyl, difluoromethyl, trifluoromethyl, 2-fluoroethyl, 2,2-difluoroethyl, 2,2,2-trifluoroethyl, 1,1,2,2-tetrafluoroethyl, 3,3,3-trifluoropropyl, 1-methyl-2-fluoroethyl, 1-methyl-2,2-difluoroethyl, 1-methyl-2,2,2-trifluoroethyl and 1,1,1,3,3,3-hexafluoropropan-2-yl.

As used herein, $C_1$-$C_3$ alkoxy is a straight-chain or branched alkyl group having 1, 2 or 3 carbon atoms which is bound to the remainder of the molecule via an oxygen atom. Examples of such a group are methoxy and ethoxy.

As used herein, fluorinated $C_1$-$C_3$ alkoxy is a $C_1$-$C_3$alkoxy group as defined above, wherein at least one, e.g. 1, 2, 3, 4 or 5 hydrogen atoms are replaced by fluorine atoms. Examples of such a group are fluoromethoxy, difluoromethoxy, trifluoromethoxy, 2-fluoroethoxy, 2,2-difluoroethoxy, 2,2,2-trifluoroethoxy and 1,1,2,2-tetrafluoroethoxy.

As used herein, $C_3$-$C_6$ cycloalkyl is a cycloaliphatic radical having 3 to 6 ring-carbon atoms, examples being cyclopropyl, cyclobutyl, cyclopentyl and cyclohexyl.

As used herein, fluorinated $C_3$-$C_6$ cycloalkyl is a cycloaliphatic radical having 3 to 6 ring-carbon atoms as defined above, wherein at least one, e.g. 1, 2, 3, 4 or 5 hydrogen atoms are replaced by fluorine atoms. Examples of such a group are 1-fluorocyclopropyl, 2-fluorocyclopropyl, 2,2-difluorocyclopropyl, 1-fluorocyclobutyl, 2-fluorocyclobutyl, 2,2-difluorocyclobutyl, 3-fluorocyclobutyl, 2,3-difluorocyclobutyl, 3,3-difluorocyclobutyl etc.

A saturated or unsaturated hydrocarbon chain having a chain length of 4 to 6 includes 1,4-, 1,5- and 1,6-alkanediyl such as butan-1,4-diyl, pentan-1,5-diyl and hexan-1,6-diyl as well as 1,4-, 1,5- and 1,6-alkenediyl such as but-2-en-1,4-diyl, pent-2-en-1,5-diyl, hex-2-en-1,6-diyl and hex-3-en-1,6-diyl, where the unsaturated hydrocarbon chain having a chain length of 4 to 6 may be unsubstituted or substituted by 1, 2 or 3 methyl groups such as in 1-methylbutan-1,4-diyl, 1-methylpentan-1,5-diyl, 1-methylhexan-1,6-diyl, 1,1-dimethylbutan-1,4-diyl, 1,1-dimethylpentan-1,5-diyl, 1,1-dimethylhexan-1,6-diyl, 2-methylbutan-1,4-diyl, 2-methylpentan-1,5-diyl, 3-methylpentan-1,5-diyl, 2-methylhexan-1,6-diyl, 3-methylhexan-1,6-diyl, 2,2-dimethylbutan-1,4-diyl, 2-methylbut-2-en-1,4-diyl, 2-methylpent-2-en-1,5-diyl, 2-methylpent-3-en-1,5-diyl etc.

A preferred embodiment of the relates to compounds of the formula I, to the pharmaceutically acceptable salts and to the N-oxides thereof, wherein A is selected from the group consisting of $(CH_2)_4$, $CH_2$—$CH_2$—$CH(CH_3)$—$CH_2$, $CH_2$—CH$(CH_3)$—$CH_2$—$CH_2$, cis $CH_2$—CH=CH—$CH_2$, trans $CH_2$—CH=CH—$CH_2$, cis $CH_2$—CH=C$(CH_3)$—$CH_2$, trans $CH_2$—CH=C$(CH_3)$—$CH_2$, cis $CH_2$—C$(CH_3)$=CH—$CH_2$ and trans $CH_2$—C$(CH_3)$=CH—$CH_2$, in particular $(CH_2)_4$.

A preferred embodiment of the invention relates to compounds of the formula I, to the pharmaceutically acceptable salts and to the N-oxides thereof, wherein $R^1$ is hydrogen.

A preferred embodiment of the invention relates to compounds of the formula I, to the pharmaceutically acceptable salts and to the N-oxides thereof, wherein $R^2$ is selected from the group consisting hydrogen, methyl, ethyl, fluorinated $C_1$-alkyl, fluorine or chlorine. In a particular embodiment of the invention $R^2$ is hydrogen. In another particular embodiment of the invention $R^2$ is methyl.

A preferred embodiment of the invention relates to compounds of the formula I, to the pharmaceutically acceptable salts and to the N-oxides thereof, wherein $R^3$ is branched $C_4$-$C_6$-alkyl, in particular tert.-butyl.

A preferred embodiment of the invention relates to compounds of the formula I, to the pharmaceutically acceptable salts and to the N-oxides thereof, wherein $R^4$ is fluorinated $C_1$-$C_2$-alkyl, n-propyl, n-butyl, tert-butyl or cyclobutyl, in particular fluorinated $C_1$-alkyl, more preferably trifluoromethyl.

Amongst the compounds of the present invention, more preference is given to those, where in formula I at least two, in particular at least 3 and especially at least 4 of the variables A, $R^1$, $R^2$, $R^3$, $R^4$ have the meanings given as preferred meanings.

A particular preferred embodiment of the invention relates to compounds of the formula I, to the pharmaceutically acceptable salts and to the N-oxides thereof, wherein the variables A, $R^1$, $R^2$, $R^3$, $R^4$ the following meanings:
A is $(CH_2)_4$, $CH_2$—$CH_2$—$CH(CH_3)$—$CH_2$, $CH_2$—$CH(CH_3)$—$CH_2$—$CH_2$, cis $CH_2$—$CH$=$CH$—$CH_2$, trans $CH_2$—$CH$=$CH$—$CH_2$, cis $CH_2$—$CH$=$C(CH_3)$—$CH_2$, trans $CH_2$—$CH$=$C(CH_3)$—$CH_2$, cis $CH_2$—$C(CH_3)$=$CH$—$CH_2$, trans $CH_2$—$C(CH_3)$=$CH$—$CH_2$, in particular $(CH_2)_4$.
$R^1$ is hydrogen;
$R^2$ is hydrogen, methyl, ethyl, fluorinated $C_1$-alkyl, fluorine or chlorine, in particular hydrogen or methyl;
$R^3$ is branched $C_4$-$C_6$-alkyl, in particular tert.-butyl; and
$R^4$ is fluorinated $C_1$-$C_2$-alkyl, n-propyl, n-butyl, tert-butyl or cyclobutyl, preferably fluorinated $C_1$-alkyl, in particular trifluoromethyl.

Amongst the compounds of the present invention, more preference is given to those, where in formula I the variables A, $R^1$, $R^2$, $R^3$, $R^4$ have the following meanings:
A is $(CH_2)_4$, $CH_2$—$CH_2$—$CH(CH_3)$—$CH_2$, $CH_2$—$CH(CH_3)$—$CH_2$—$CH_2$, cis $CH_2$—$CH$=$CH$—$CH_2$, trans $CH_2$—$CH$=$CH$—$CH_2$, cis $CH_2$—$CH$=$C(CH_3)$—$CH_2$, trans $CH_2$—$CH$=$C(CH_3)$—$CH_2$, cis $CH_2$—$C(CH_3)$=$CH$—$CH_2$, trans $CH_2$—$C(CH_3)$=$CH$—$CH_2$, in particular $(CH_2)_4$;
$R^1$ is hydrogen;
$R^2$ is hydrogen;
$R^3$ is branched $C_4$-$C_6$-alkyl, in particular tert.-butyl; and
$R^4$ is fluorinated $C_1$-$C_2$-alkyl, n-propyl, n-butyl, tert-butyl or cyclobutyl, preferably fluorinated $C_1$-$C_2$-alkyl, in particular trifluoromethyl.

Amongst the compounds of the present invention, likewise more preference is given to those, where in formula I the variables A, $R^1$, $R^2$, $R^3$, $R^4$ have the following meanings:
A is $(CH_2)_4$, $CH_2$—$CH_2$—$CH(CH_3)$—$CH_2$, $CH_2$—$CH(CH_3)$—$CH_2$—$CH_2$, cis $CH_2$—$CH$=$CH$—$CH_2$, trans $CH_2$—$CH$=$CH$—$CH_2$, cis $CH_2$—$CH$=$C(CH_3)$—$CH_2$, trans $CH_2$—$CH$=$C(CH_3)$—$CH_2$, cis $CH_2$—$C(CH_3)$=$CH$—$CH_2$, trans $CH_2$—$C(CH_3)$=$CH$—$CH_2$, in particular $(CH_2)_4$;
$R^1$ is hydrogen;
$R^2$ is methyl;
$R^3$ is branched $C_4$-$C_6$-alkyl, in particular tert.-butyl; and
$R^4$ is fluorinated $C_1$-$C_2$-alkyl, n-propyl, n-butyl, tert-butyl or cyclobutyl, preferably fluorinated $C_1$-$C_2$-alkyl, in particular trifluoromethyl.

Amongst the compounds of the present invention, likewise more preference is given to those, where in formula I the variables A, $R^1$, $R^2$, $R^3$, $R^4$ have the following meanings:
A is $(CH_2)_4$;
$R^1$ is hydrogen;
$R^2$ is hydrogen, methyl, ethyl, fluorinated $C_1$-alkyl, fluorine or chlorine, in a particular hydrogen or methyl;
$R^3$ is branched $C_4$-$C_6$-alkyl, in particular tert.-butyl; and
$R^4$ is fluorinated $C_1$-$C_2$-alkyl, n-propyl, n-butyl, tert-butyl or cyclobutyl, preferably fluorinated $C_1$-alkyl, in particular trifluoromethyl.

Amongst the compounds of the present invention, likewise more preference is given to those, where in formula I the variables A, $R^1$, $R^2$, $R^3$, $R^4$ have the following meanings:
A is $(CH_2)_4$, $CH_2$—$CH_2$—$CH(CH_3)$—$CH_2$, $CH_2$—$CH(CH_3)$—$CH_2$—$CH_2$, cis $CH_2$—$CH$=$CH$—$CH_2$, trans $CH_2$—$CH$=$CH$—$CH_2$, cis $CH_2$—$CH$=$C(CH_3)$—$CH_2$, trans $CH_2$—$CH$=$C(CH_3)$—$CH_2$, cis $CH_2$—$C(CH_3)$=$CH$—$CH_2$, trans $CH_2$—$C(CH_3)$=$CH$—$CH_2$, in particular $(CH_2)_4$;
$R^1$ is hydrogen;
$R^2$ is hydrogen, methyl, ethyl, fluorinated $C_1$-alkyl, fluorine or chlorine, in particular hydrogen or methyl;
$R^3$ is tert.-butyl; and
$R^4$ is fluorinated $C_1$-$C_2$-alkyl, n-propyl, n-butyl, or cyclobutyl, tert-butyl, preferably fluorinated $C_1$-alkyl, in particular trifluoromethyl.

Amongst the compounds of the present invention, likewise more preference is given to those, where in formula I the variables A, $R^1$, $R^2$, $R^3$, $R^4$ have the following meanings:
A is $(CH_2)_4$, $CH_2$—$CH_2$—$CH(CH_3)$—$CH_2$, $CH_2$—$CH(CH_3)$—$CH_2$—$CH_2$, cis $CH_2$—$CH$=$CH$—$CH_2$, trans $CH_2$—$CH$=$CH$—$CH_2$, cis $CH_2$—$CH$=$C(CH_3)$—$CH_2$, trans $CH_2$—$CH$=$C(CH_3)$—$CH_2$, cis $CH_2$—$C(CH_3)$=$CH$—$CH_2$, trans $CH_2$—$C(CH_3)$=$CH$—$CH_2$, in particular $(CH_2)_4$;
$R^1$ is hydrogen;
$R^2$ is hydrogen, methyl, ethyl, fluorinated $C_1$-alkyl, fluorine or chlorine, in particular hydrogen or methyl;
$R^3$ is branched $C_4$-$C_6$-alkyl, in particular tert.-butyl; and
$R^4$ is fluorinated $C_1$-alkyl, in particular trifluoromethyl.

Amongst the compounds of the present invention, likewise more preference is given to those, where in formula I the variables A, $R^1$, $R^2$, $R^3$, $R^4$ have the following meanings:
A is $(CH_2)_4$,
$R^1$ is hydrogen;
$R^2$ is hydrogen or methyl, in particular hydrogen;
$R^3$ is branched $C_4$-$C_6$-alkyl, in particular tert.-butyl; and
$R^4$ is fluorinated $C_1$-$C_2$-alkyl, n-propyl, n-butyl, tert-butyl or cyclobutyl, preferably fluorinated $C_1$-alkyl, in particular trifluoromethyl.

Examples of compounds according to the present invention include

2-{4-[4-(2-tert-Butyl-6-trifluoromethyl-pyrimidin-4-yl)-piperazin-1-yl]butyl}-2H-[1,2,4]triazine-3,5-dione 2-{4-[4-(2-tert-Butyl-6-propyl-pyrimidin-4-yl)-piperazin-1-yl]butyl}-2H-[1,2,4]triazine-3,5-dione 2-{4-[4-(2,6-Di-tert-butyl-pyrimidin-4-yl)-piperazin-1-yl]butyl}-2H-[1,2,4]triazine-3,5-dione 2-{4-[4-(2-tert-Butyl-6-cyclobutyl-pyrimidin-4-yl)-piperazin-1-yl]butyl}-2H-[1,2,4]triazine-3,5-dione 2-{4-[4-(2-tert-Butyl-6-trifluoromethyl-pyrimidin-4-yl)-piperazin-1-yl]butyl}-6-methyl-2H-[1,2,4]triazine-3,5-dione hydrochloride 2-{4-[4-(2-tert-Butyl-6-propyl-pyrimidin-4-yl)-piperazin-1-yl]butyl}-6-methyl-2H-[1,2,4]triazine-3,5-dione hydrochloride 2-{4-[4-(2-tert-Butyl-6-trifluoromethyl-pyrimidin-4-yl)-piperazin-1-yl]butyl}-4-methyl-2H-[1,2,4]triazine-3,5-dione and the pharmacologically tolerated salts thereof and the tautomers thereof.

The compounds I according to the invention are prepared in analogy with methods known from the literature. An important approach to the compounds according to the invention is offered by the reaction of a 2-substituted 1,2,4-triazine-3,4-dione compound II with an 4-piperazine-1yl-pyrimidine compound III as depicted in scheme 1.

Scheme 1:

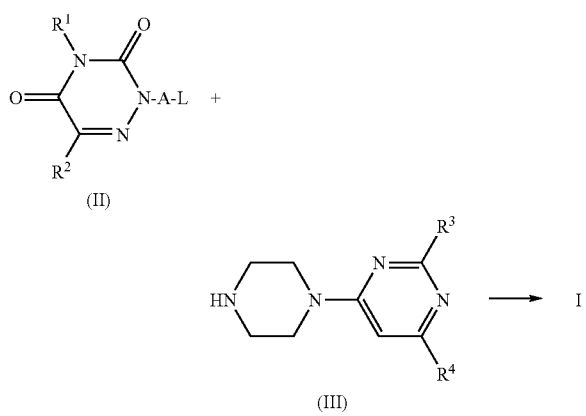

In scheme 1, $R^1$, $R^2$, $R^3$, $R^4$ and A have the aforementioned meanings. L is a leaving group which can be displaced nucleophilically. Examples of suitable leaving groups which can be displaced nucleophilically are chlorine, bromine or iodine, alkyl- and aryl-sulfonate such as mesylate, tosylate. The reaction conditions necessary for the reaction correspond to the reaction conditions usual for nucleophilic substitutions. The reaction conditions are similar to those described in WO 2004/080981 and WO 2005/118558 and can be taken therefrom or from the working examples of the present application.

The compounds of the formula II, wherein $R^1$ is hydrogen, can be prepared by reacting a protected 3,5-bishydroxy-1,2,4-triazine compound of the formula IV with a compound L'-A-L, wherein A is as defined above and L and L' are leaving groups which can be displaced nucleophilically.

Scheme 2:

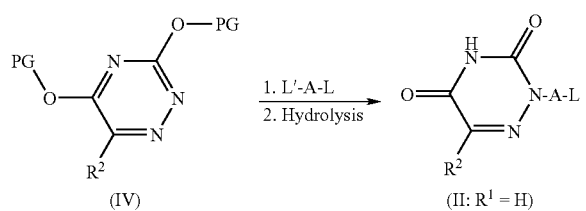

In scheme 2, $R^2$ and A have the aforementioned meanings. Examples of suitable leaving groups which can be displaced nucleophilically are the leaving groups mentioned in scheme 1. L and L' are preferably different from one another and differ in reactivity. For example, L' is bromine or iodine and L is chlorine. PG is an OH-protecting group, which can be cleaved by hydrolysis, e.g. trialkylsilyl such as trimethylsilyl, or $C_2$-$C_4$-allyldimethylsilyl.

The reaction conditions necessary for the reaction according to step 1 of scheme 2 correspond to the reaction conditions usual for nucleophilic substitutions. The reaction conditions are similar to those described in WO 2004/080981 and WO 2005/118558 and can be taken therefrom or from the working examples of the present application. Hydrolysis can be simply achieved by reacting the reaction mixture obtained from the reaction of compound IV with compound L'-A-L with water. Thereby the compound of the formula II is obtained, wherein $R^1$ is hydrogen. This compound II may be reacted with an alkylating agent to introduce a radical $R^1$ which is different from hydrogen.

Alternatively, compounds II can be prepared by the method described in U.S. Pat. No. 5,977,106.

Compounds of the formula III are well known, e.g. from WO 99/02503, WO 2004/080981, WO2004/108706, WO 2005/118558, WO 2005/118571 and WO 2006/015842 or can be prepared by the methods described therein.

Compounds of the formula IV are e.g. known from (i) Tann et al., J. Org. Chem. (1985), 3644-3647, (ii) Singh et al., Synthesis (1990), 520-522, or can be prepared starting from the corresponding 1,2,4-triazin-3,5-dion using conventional methods of O-protection as described e.g. in P. J. Kocienski, "Protecting Groups", $2^{nd}$ ed. Georg Thieme Verlag Stuttgart 2000, pp 28 to 41 and the literature cited therein.

The N-oxides of compounds of formula I can be obtained by treating a compound of the formula I with an oxidizing agent, in particular an inorganic or organic peroxide or hydroperoxide, such as hydrogen peroxide, or percarboxylic acids, such as peracetic acid, perbenzoic acid or m-chloroperbenzoic acid.

If not otherwise indicated, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002).

Examples of solvents which can be used are ethers such as diethyl ether, diisopropyl ether, methyl tert-butyl ether or tetrahydrofuran, aprotic polar solvents such as dimethylformamide, dimethyl sulfoxide, dimethoxyethane and acetonitrile, aromatic hydrocarbons such as toluene and xylene, ketones such as acetone or methyl ethyl ketone, halohydrocarbons such as dichloromethane, trichloromethane and dichloroethane, esters such as ethyl acetate and methyl butyrate, carboxylic acids such as acetic acid or propionic acid, and alcohols such as methanol, ethanol, n-propanol, isopropanol and butanol.

If desired, it is possible for a base to be present in order to neutralize protons which are released in the reactions. Suitable bases include inorganic bases such as sodium carbonate, potassium carbonate, sodium hydrogen carbonate or potassium hydrogen carbonate, alkoxides such as sodium methoxide or sodium ethoxide, alkali metal hydrides such as sodium hydride, organometallic compounds such as butyllithium compounds or alkylmagnesium compounds, and organic nitrogen bases such as triethylamine or pyridine. The latter compounds can at the same time serve as solvents.

The crude product is isolated in a customary manner, as for example by filtering, distilling off the solvent or extracting from the reaction mixture, etc. The resulting compounds can be purified in a customary manner, as for example by means of recrystallizing from a solvent, by means of chromatography or by means of converting into an acid addition salt.

The acid addition salts are prepared in a customary manner by mixing the free base with a corresponding acid, where appropriate in solution in an organic solvent as for example a lower alcohol such as methanol, ethanol, n-propanol or isopropanol, an ether such as methyl tert-butyl ether or diisopropyl ether, a ketone such as acetone or methyl ethyl ketone, or an ester such as ethyl acetate. For example, the free base of formula I and suitable amounts of the corresponding acid, such as from 1 to 4 moles per mol of formula I, are dissolved in a suitable solvent, preferably in a lower alcohol such as methanol, ethanol, n-propanol or isopropanol. Heating may be applied to dissolve the solids, if necessary. Solvents, wherein the acid addition salt of I is insoluble (anti-solvents), might be added to precipitate the salt. Suitable anti-solvents comprise $C_1$-$C_4$-alkylesters of $C_1$-$C_4$-aliphatic acids such as ethyl acetate, aliphatic and cycloaliphatic hydrocarbons such as hexane, cyclohexane, heptane, etc., di-$C_1$-$C_4$-alkylethers such as methyl tert-butyl ether or diisopropyl ether. A part or all of the anti-solvent may be added to the hot solution of the salt and the thus obtained solution is cooled; the remainder of the anti-solvent is then added until the concentration of the salt in the mother liquor is as low as approximately 10 mg/l or lower.

The compounds according to the invention of the formula I are surprisingly highly selective dopamine $D_3$ receptor ligands. Because of their low affinity for other receptors such as $D_1$ receptors, $D_4$ receptors, α1-adrenergic and/or α2-adrenergic receptors, muscarinergic receptors, histamine receptors, opiate receptors and, in particular, dopamine $D_2$ receptors, the compounds can be expected to give rise to fewer side-effects than do the classic neuroleptics, which are $D_2$ receptor antagonists.

The high affinity of the compounds according to the invention for $D_3$ receptors is reflected in very low in-vitro $K_i$ values of as a rule less than 100 nM (nmol/l), preferably of less than 50 nM and, in particular of less than 10 nM. The displacement of [$^{125}$I]-iodosulpride can, for example, be used in receptor binding studies for determining binding affinities for $D_3$ receptors.

The selectivity of the compounds of the invention for the $D_2$ receptor relative to the $D_3$ receptor, expressed as $K_i(D_2)$/$K_i(D_3)$, is as a rule at least 20, preferably at least 50. The displacement of [$^3$]SCH23390, [$^{125}$I] iodosulpride or [$^{125}$I] spiperone can be used, for example, in carrying out receptor binding studies on $D_1$, $D_2$ and $D_4$ receptors.

Because of their binding profile, the compounds can be used for treating diseases or disorders which respond to dopamine $D_3$ ligands, that is, they can be expected to be effective for treating those medical disorders or diseases in which exerting an influence on (modulating) the dopamine $D_3$ receptors leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorders" denotes disturbances and/or anomalies which are as a rule regarded as being pathological conditions or functions and which can manifest themselves in the form of particular signs, symptoms and/or malfunctions.

While the treatment according to the invention can be directed toward individual disorders, that is, anomalies or pathological conditions, it is also possible for several anomalies, which may be causatively linked to each other, to be combined into patterns or syndromes which can be treated in accordance with the invention.

The disorders which can be treated in accordance with the invention are, in particular, psychiatric and neurological disturbances. These disturbances include, in particular, organic disturbances, including symptomatic disturbances such as psychoses of the acute exogenous reaction type or attendant psychoses of organic or exogenous cause as for example in association with metabolic disturbances, infections and endocrinopathies; endogenous psychoses such as schizophrenia and schizotype and delusional disturbances; affective disturbances such as depressions, major depressive disorder, mania and/or manic-depressive conditions; mixed forms of the above-described disturbances; neurotic and somatoform disturbances and also disturbances in association with stress; dissociative disturbances such as loss of consciousness, clouding of consciousness, double consciousness and personality disturbances; autism; disturbances in attention and waking/sleeping behavior such as behavioral disturbances and emotional disturbances whose onset lies in childhood and youth as for example hyperactivity in children, intellectual deficits such as attention disturbances (attention deficit disorders with or without hyperactivity), memory disturbances and cognitive disturbances such as impaired learning and memory (impaired cognitive function), dementia, narcolepsy and sleep disturbances such as restless legs syndrome; development disturbances; anxiety states; delirium; sexual disturbances such as impotence in men; eating disturbances such as anorexia or bulimia; addiction; bipolar disorder; and other unspecified psychiatric disturbances.

The disorders which can be treated in accordance with the invention also include Parkinson's disease and epilepsy and, in particular, the affective disturbances connected thereto.

Also treatable are addictive diseases (substance abuse), that is, psychic disorders and behavioral disturbances which are caused by the abuse of psychotropic substances such as pharmaceuticals or narcotics, and also other addiction behaviors such as addiction to gaming and/or impulse control disorders not elsewhere classified. Examples of addictive substances include opioids such as morphine, heroin and codeine: cocaine; nicotine; alcohol; substances which interact with the GABA chloride channel complex; sedatives, hypnotics and tranquilizers as for example benzodiazepines; LSD; cannabinoids; psychomotor stimulants such as 3,4-methylenedioxy-N-methylamphetamine (ecstasy); amphetamine and amphetamine-like substances such as methylphenidate; and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of dopamine $D_3$ receptors.

According to another aspect of the present invention, the treatment is directed, in particular, toward those disorders which can be influenced, within the sense of an expedient medicinal treatment, by the binding of preferably exogeneously administered binding partners (ligands) to dopamine $D_3$ receptors.

The diseases which can be treated with the compounds according to the invention are frequently characterized by progressive development, that is, the above-described conditions change over the course of time; as a rule, the severity increases and conditions may possibly merge into each other or other conditions may appear in addition to those which already exist.

The compounds according to the invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, such as Huntington's chorea and Gilles-de-la-Tourette's syndrome, vertigo syndromes such as peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, as for example for the suppression of symptoms. It can be effected over a short period, be orientated over the medium term or can be a long-term treatment, as for example within the context of a maintenance therapy.

Surprisingly, high brain levels in excess of 1000 ng/g, in particular in excess of 3000 ng/g (determined in rats as the value $C_{max}$) can be achieved when administering the compounds of the invention. Thus, the compounds of the present invention show a better bioavailabilty.

Therefore the compounds according to the invention are preferentially suitable for treating diseases of the central nervous system, in particular for treating affective disorders; neurotic disturbances, stress disturbances and somatoform disturbances and psychoses, and, in particular, for treating schizophrenia and bipolar disorder.

Because of their high selectivity with regard to the $D_3$ receptor, the compounds I according to the invention are also suitable for treating disturbances of kidney function, in particular disturbances of kidney function which are caused by diabetes (see WO 00/67847) and, especially, diabetic nephropathy.

In addition, compounds of the present invention may possess other pharmacological and/or toxicological properties that render them especially suitable for development as pharmaceuticals. As an example, compounds of formula I having a low affinity for the HERG receptor could be expected to have a reduced likelihood of inducing QT-prolongation (regarded as a one predictor of risk of causing cardiac arrythmia. (For a discussion of QT-prolongation see for example A. Cavalli et al., *J. Med. Chem.* 2002, 45:3844-3853 and the literature cited therein; a HERG assay is commercially available from GENION Forschungsgesellschaft mbH, Hamburg, Germany).

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.01 to 1000 mg/kg, more preferably from 0.1 to 1000 mg/kg of bodyweight in the case of oral administration, or of from about 0.01 to 100 mg/kg, more preferably from 0.1 to 100 mg/kg of bodyweight in the case of parenteral administration, is supplied to an individual to be treated.

The invention also relates to the production of pharmaceutical compositions for treating an individual, preferably a mammal and in particular a human being, a farm animal or a domestic animal. Thus, the compounds are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms such as powders, granules, tablets (in particular film tablets), lozenges, sachets, cachets, sugar-coated tablets, capsules such as hard gelatin capsules and soft gelatin capsules; suppositories or vaginal medicinal forms; semisolid medicinal forms such as ointments, creams, hydrogels, pastes or plasters; and also liquid medicinal forms such as solutions, emulsions (in particular oil-in-water emulsions), suspensions such as lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are usually mixed or diluted with an excipient. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the invention without limiting it.

The compounds were either characterized via proton-NMR in $d_6$-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

PREPARATION EXAMPLES

I. Preparation of Intermediate Compounds II

Preparation Example 1

3,5-Bis-trimethylsilanyloxy-[1,2,4]triazine

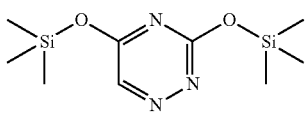

1.7 mL of trimethylchlorosilane (13.27 mmol) were added with stirring to a mixture of 15 g (133 mmol) of 2H-[1,2,4]triazine-3,5-dione and 74.7 mL of hexamethyldisilazane (358 mmol). The mixture was stirred for 2 h under reflux, and excess of reagents removed in high vacuo. The forming white solid was directly used in the next step.

$^1$H-NMR (DMSO-d$_6$, 400 MHz): δ [ppm] 7.35 (s, 1H), −0.05 (s, 18H).

Preparation Example 2

2-(4-Chloro-butyl)-2H-[1,2,4]triazine-3,5-dione

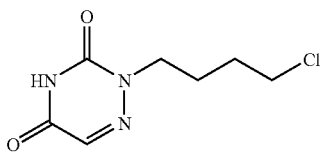 [SMILES: O=c1cnn(CCCCCl)c(=O)[nH]1]

22.1 g of 3,5-Bis-trimethylsilanyloxy-[1,2,4]triazine (86 mmol) were dissolved in 150 mL of dichloroethane followed by addition of 14.7 g of 1-bromo-4-chloro-butane (86 mmol) and 0.218 g of iodine (0.858 mmol). The reaction mixture was stirred for 25 h at room temperature. Then, 300 mL of methanol were added and the mixture was stirred for an additional 10 minutes. The solvents were evaporated under reduced pressure and the residue was partitioned between dichloromethane and water. The aqueous phase was extracted several times with dichloromethane. The combined organic layers were washed with 10% aqueous sodium bicarbonate solution and saturated aqueous sodium chloride solution, dried over sodium sulfate, filtered, and the organic phase was evaporated under reduced pressure. The thus obtained crude product was purified via silica gel chromatography using dichloromethane-methanol 0-10% to yield 13.4 g of the desired product.

ESI-MS: 204.1 [M+H]$^+$ $^1$H-NMR (CDCl$_3$, 400 MHz): δ [ppm] 9.7 (s, broad, 1H), 7.4 (s, 1H), 4.0 (m, 2H), 3.6 (m, 2H), 1.95 (m, 2H), 1.85 (m, 2H).

Preparation Example 3

2-(4-Chloro-butyl)-6-methyl-2H-[1,2,4]triazine-3,5-dione

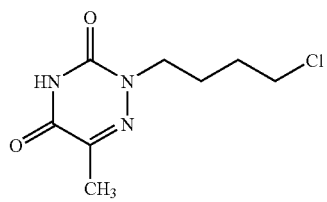

2-(4-Chloro-butyl)-6-methyl-2H-[1,2,4]triazine-3,5-dione were synthesized as described for the synthesis of 2-(4-Chloro-butyl)-2H-[1,2,4]triazine-3,5-dione starting from 6-methyl-2H-[1,2,4]triazine-3,5-dione which was converted into 6-methyl-3,5-bis-trimethylsilanyloxy-[1,2,4]triazine by the method described in working example 1 and thereafter reacted with 1-bromo-4-chloro-butane according to working example 2.

ESI-MS: 218.1 [M+H]$^+$ $^1$H-NMR (CDCl$_3$, 400 MHz): δ [ppm] 9.7 (s, broad, 1H), 3.95 (m, 2H), 3.6 (m, 2H), 2.25 (s, 3H), 1.9 (m, 2H), 1.8 (m, 2H).

II. Preparation of the Compounds I

Example 1

2-{4-[4-(2-tert-Butyl-6-trifluoromethyl-pyrimidin-4-yl)-piperazin-1-yl]butyl}-2H-[1,2,4]triazine-3,5-dione hydrochloride 13.4 g of 2-(4-chloro-butyl)-2H-[1,2,4]triazine-3,5-dione (65.8 mmol) and 18.97 g of 2-tert-butyl-4-piperazin-1-yl-6-trifluoromethyl-pyrimidine (65.8 mmol) were dissolved in 400 mL of dimethylformamide. After addition of 33.9 g of sodium bromide (329 mmol) and 115 mL of N,N-diisopropylethylamine (658 mmol), the reaction was stirred for 48 h at room temperature. Then the solvent was removed under reduced pressure and the obtained residue was triturated with 400 mL of ethyl acetate and the obtained solution was filtered. The filtrate was evaporated to dryness and the remaining oily residue was treated with 100 mL of diethyl ether, filtered and the filtrate was again evaporated to dryness. The crude product was purified three times via silica gel chromatography (ethyl acetate-methanol 0-100%; dichloromethane-methanol 0-5%; dichloro-methane-methanol 0-2%) to yield the free base of the title compound. This product was transferred into its hydrochloride salt via treatment with HCl/diethyl ether (yield 2.56 g).

ESI-MS: 456.3 [M+H]$^+$ $^1$H-NMR (DMSO-d$_6$, 400 Hz): δ [ppm] 12.15 (s, broad, 1H), 11.7 (s, broad, 1H), 7.45 (s, 1H), 7.2 (s, 1H), 4.65 (m, broad, 2H), 3.85 (m, 2H), 3.45-3.65 (m, 4H), 3.0-3.15 (m, 4H), 1.8 (m, 2H), 1.7 (m, 2H), 1.3 (s, 9H).

Example 2

2-{4-[4-(2-tert-Butyl-6-difluoromethyl-pyrimidin-4-yl)-piperazin-1-yl]butyl}-2H-[1,2,4]triazine-3,5-dione hydrochloride 2-{4-[4-(2-tert-Butyl-6-difluoromethyl-pyrimidin-4-yl)-piperazin-1-yl]butyl}-2H-[1,2,4]triazine-3,5-dione hydrochloride was prepared from 2-(4-chloro-butyl)-2H-[1,2,4]triazine-3,5-dione and 2-tert-butyl-4-piperazin-1-yl-6-difluoromethyl-pyrimidine by analogy to the process described in example 1 using N-methyl-pyrrolidine as solvent.
ESI-MS: 438.2 [M+H]$^+$
$^1$H-NMR (DMSO-d$^6$, 400 Hz): δ [ppm] 12.15 (s, broad, 1H), 9.6 (s, broad, 1H), 7.5 (s, 1H), 7.0 (s, 1H), 6.75 (t, 1H, CHF2), 3.0-4.7 (several m, 12H), 1.7 (m, 4H), 1.3 (s, 9H).

Example 3

2-{4-[4-(2-tert-Butyl-6-propyl-pyrimidin-4-yl)-piperazin-1-yl]butyl}-2H-[1,2,4]triazine-3,5-dione 2-{4-[4-(2-tert-Butyl-6-propyl-pyrimidin-4-yl)-piperazin-1-yl]butyl}-2H-[1,2,4]triazine-3,5-dione was prepared from 2-(4-chloro-butyl)-2H-[1,2,4]triazine-3,5-dione and 2-tert-butyl-4-piperazin-1-yl-6-propylpyrimidine by analogy to the process described in example 1.
ESI-MS: 430.3 [M+H]$^+$
$^1$H-NMR (CDCl$_3$, 400 Hz): δ [ppm] 7.45 (s, 1H), 6.1 (s, 1H), 4.0 (m, 2H), 3.65 (m, 4H), 2.55 (m, 6H), 2.45 (m, 2H), 1.8 (m, 2H), 1.7 (m, 2H), 1.6 (m, 2H), 1.3 (s, 9H), 0.95 (t, 3H).

Example 4

2-{4-[4-(2,6-Di-tert-butyl-pyrimidin-4-yl)-piperazin-1-yl]butyl}-2H-[1,2,4]triazine-3,5-dione trifluoroacetate 2-{4-[4-(2,6-di-tert-Butyl-pyrimidin-4-yl)-piperazin-1-yl]butyl}-2H-[1,2,4]triazine-3,5-dione was prepared from 2-(4-chloro-butyl)-2H-[1,2,4]triazine-3,5-dione and 2,6-di-tert-butyl-4-piperazin-1-ylpyrimidine by analogy to the process described in example 1. The trifluoroacetate salt was obtained after lyophilization of material obtained from HPLC purification run with 0.1% trifluoroacetic acid.
ESI-MS: 444.4 [M+H]$^+$
$^1$H-NMR (DMSO-d$_6$, 400 Hz): δ [ppm] 12.15 (s, broad, 1H), 9.9 (s, broad, 1H), 7.5 (s, 1H), 6.6 (s, 1H), 4.6 (m, 2H), 3.9 (m, 2H), 3.3-3.7 (m, 2H), 3.1-3.3 (several m, 4H), 3.05 (m, 2H), 1.7 (m, 4H), 1.3 (s, 9H), 1.25 (s, 9H).

Example 5

2-{4-[4-(2-tert-Butyl-6-cyclobutyl-pyrimidin-4-yl)-piperazin-1-yl]butyl}-2H-[1,2,4]triazine-3,5-dione 2-{4-[4-(2-tert-Butyl-6-cyclobutyl-pyrimidin-4-yl)-piperazin-1-yl]butyl}-2H-[1,2,4]triazine-3,5-dione was prepared from 2-(4-chloro-butyl)-2H-[1,2,4]triazine-3,5-dione and 2-tert-butyl-4-piperazin-1-yl-6-cyclobutylpyrimidine by analogy to the process described in example 1.
ESI-MS: 442.3 [M+H]$^+$
$^1$H-NMR (CDCl$_3$, 400 Hz): δ [ppm] 7.35 (s, 1H), 6.1 (s, 1H), 4.0 (m, 2H), 3.65 (m, 4H), 3.4 (m, 1H), 2.55 (m, 4H), 2.45 (m, 2H), 2.3 (m, 4H), 2.0 (m, 1H), 1.9 (m, 1H), 1.8 (m, 2H), 1.6 (m, 2H), 1.35 (s, 9H).

Example 6

2-{4-[4-(2-tert-Butyl-6-trifluoromethyl-pyrimidin-4-yl)-piperazin-1-yl]butyl}-6-methyl-2H-[1,2,4]triazine-3,5-dione hydrochloride 2-{4-[4-(2-tert-Butyl-6-trifluoromethyl-pyrimidin-4-yl)-piperazin-1-yl]-butyl}-6-methyl-2H-[1,2,4]triazine-3,5-dione hydrochloride was prepared from 2-(4-chloro-butyl)-6-methyl-2H-[1,2,4]triazine-3,5-dione and 2-tert-butyl-4-piperazin-1-yl-6-trifluoromethyl-pyrimidine by analogy to the process described in example 1.
ESI-MS: 470.2 [M+H]$^+$ Example 7

2-{4-[4-(2-tert-Butyl-6-propyl-pyrimidin-4-yl)-piperazin-1-yl]butyl}-6-methyl-2H-[1,2,4]triazine-3,5-dione hydrochloride 2-{4-[4-(2-tert-Butyl-6-propyl-pyrimidin-4-yl)-piperazin-1-yl]butyl}-6-methyl-2H-[1,2,4]triazine-3,5-dione hydrochloride was prepared from 2-(4-chloro-butyl)-6-methyl-2H-[1,2,4]triazine-3,5-dione and 2-tert-butyl-4-piperazin-1-yl-6-propyl-pyrimidine by analogy to the process described in example 1.
ESI-MS: 444.3 [M+H]$^+$
$^1$H-NMR (DMSO-d$_6$, 400 Hz): δ [ppm] 7.1 (s, 1H), 5.0 (s, broad, 1H), 4.45 (s, broad, 1H), 3.7-3.9 (m, 6H), 3.6 (m, 2H), 3.1 (m, 4H), 2.8 (m, 2H), 2.1 (s, 3H), 1.8 (m, 2H), 1.7 (m, 4H), 1.4 (s, 9H), 0.95 (t, 3H).

Example 8

2-{4-[4-(2-tert-Butyl-6-trifluoromethyl-pyrimidin-4-yl)-piperazin-1-yl]butyl}-4-methyl-2H-[1,2,4]triazine-3,5-dione 36 mg of sodium hydride were treated with n-pentane, decanted and 5 mL of N,N-dimethylformamide (DMF) were added dropwise. The solution was cooled to 0-5° C. and a solution of 2-{4-[4-(2-tert-butyl-6-trifluoromethyl-pyrimidin-4-yl)-piperazin-1-yl]butyl}-2H-[1,2,4]triazine-3,5-dione hydrochloride (0,407 mmol) in 5 mL of DMF was slowly added. After 2 h, 0.058 g iodomethane (0.407 mmol) were added, the reaction was stirred for 16 h at room temperature and 25 ml of ice water were slowly added. The reaction was evaporated to dryness, the residue dissolved in ethyl acetate and the organic layer washed several times with saturated aqueous sodium chloride solution. The organic layer was dried over sodium sulphate, filtered and the solvent evaporated. Chromatography via silica gel chromatography (Chromabond NP, dichloromethane-methane 0-10% as eluent) and preparative reversed phase HPLC yielded 0.02 g of the title compound.
ESI-MS: 470.3 [M+H]$^+$

III. Examples of Galenic Administration Forms

Tablets of the following composition are pressed on
a tablet press in the customary manner:

A) Tablets
- 40 mg of substance from Example 1
- 120 mg of corn starch
- 13.5 mg of gelatin
- 45 mg of lactose
- 2.25 mg of Aerosil ® (chemically pure silicic acid in submicroscopically fine dispersion)
- 6.75 mg of potato starch (as a 6% paste)

B) Sugar-coated tablets
- 20 mg of substance from Example 1
- 60 mg of core composition
- 70 mg of saccharification composition The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

IV. Biological Investigations

1. Receptor Binding Studies

The substance to be tested was either dissolved in methanol/Chremophor® (BASF SE) or in dimethyl sulfoxide and then diluted with water to the desired concentration.
The substance to be tested was either dissolved in methanol/Chremophor® (BASFSE) or in dimethyl sulfoxide and then diluted with water to the desired concentration.

a) Dopamine $D_3$ Receptor:

The assay mixture (0.250 ml) was composed of membranes derived from ~$10^6$ HEK-293 cells possessing stably expressed human dopamine $D_3$ receptors, 0.1 nM [$^{125}$I]-iodosulpride and incubation buffer (total binding) or, in addition, test substance (inhibition curve) or 1 µM spiperone (nonspecific binding). Each as-say mixture was run in triplicate.

The incubation buffer contained 50 mM tris, 120 mM NaCl, 5 mM KCl, 2 mM $CaCl_2$, 2 mM $MgCl_2$ and 0.1% bovine serum albumin, 10 µM quinolone and 0.1% ascorbic acid (prepared fresh daily). The buffer was adjusted to pH 7.4 with HCl.

b) Dopamine $D_{2L}$ Receptor:

The assay mixture (1 ml) was composed of membranes from ~$10^6$ HEK-293 cells possessing stably expressed human dopamine $D_{2L}$ receptors (long isoform) and 0.01 nM [$^{125}$I] iodospiperone and incubation buffer (total binding) or, in addition, test substance (inhibition curve) or 1 µM haloperidol (nonspecific binding). Each assay mixture was run in triplicate.

The incubation buffer contained 50 mM tris, 120 mM NaCl, 5 mM KCl, 2 mM $CaCl_2$, 2 mM $MgCl_2$ and 0.1% bovine serum albumin. The buffer was adjusted to pH 7.4 with HCl.

c) Measurement and Analysis:

After having been incubated at 25° C. for 60 minutes, the assay mixtures were filtered through a Whatman GF/B glass fiber filter under vacuum using a cell collecting device. The filters were transferred to scintillation viols using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were converted into dpm using a standard quench series and the program belonging to the instrument.

The inhibition curves were analyzed by means of iterative nonlinear regression analysis using the Statistical Analysis System (SAS) which is similar to the "LIGAND" program described by Munson and Rodbard.

In these tests, the compounds according to the invention exhibit very good affinities for the $D_3$ receptor (<100 nM, frequently <50 nM, in particular <10 nM) and bind selectively to the $D_3$ receptor.

The results of the binding tests are given in Table 1.

$K_i(D_3)$: +++<10 nM, ++<50 nM, +<100 nM
$K_i(D_{2L})/K_i(D_3)$: +++>50, ++>20, +>10

TABLE 1

| Example | $K_i$ ($D_3$) [nM] | Selectivity vs. $D_2L$* |
|---|---|---|
| 1 | +++ | ++ |
| 2 | +++ | ++ |
| 3 | +++ | +++ |
| 4 | +++ | ++ |
| 5 | +++ | ++ |
| 6 | +++ | ++ |
| 7 | +++ | ++ |

*$K_i(D_{2L})/K_i(D_3)$

2. Determination of the Concentration of Compounds in Plasma and Brain Following Dosing of Compounds in Animals Male Sprague-Dawley rats were used in this study (2 to 4 per experiment). The animals were fasted overnight prior to dosing and throughout the duration of the study but were permitted water ad libitum.

Each rat received a 10 mg/kg (5 mL/kg) dose orally by gavage. At 0.5, 3 and 8 hours after drug administration, three animals were put under deep anesthesia using isoflurane and euthanized by bleeding (cardiac puncture) under deep isoflurane anesthesia. EDTA blood samples and brain tissue will be collected from each rat. Upon collection, the samples were promptly placed in an ice bath, and within 2 hours after sample collection, the blood was centrifuged at about 4° C. The resulting brain and plasma samples were placed in clean glass tubes and stored in a freezer until analysis.

The plasma samples were assayed for parent compound using appropriate liquid chromatography—mass spectrometry procedures. The results for compounds I are given in tables 2, and illustrate the high brain concentrations attainable with the compounds of the invention.

3. Determination of the Metabolic Stability

The metabolic stability of the compounds of the invention was determined in the following assay by analyzing the microsomal half-life. The test substances are incubated in a concentration of 0.5 µM as follows:

0.5 µM test substance is preincubated together with liver microsomes of various species (0.25 mg of protein/ml) in 0.05M potassium phosphate buffer pH 7.4 in microtiter plates at 37° C. for 5 min. The reaction is started by adding NADPH (1 mg/mL). Aliquots are taken after 0, 5, 10, 15, 20 and 30 min, and the reaction is stopped with the same volume of acetonitrile and cooled down. The remaining test compound concentrations are being determined by liquid chromatography—mass spectrometry analysis. Intrinsic clearance values are calculated using the elimination rate constant of test compound depletion.

We claim:

1. A 1,2,4-triazin-3,5-dione compound of the formula I

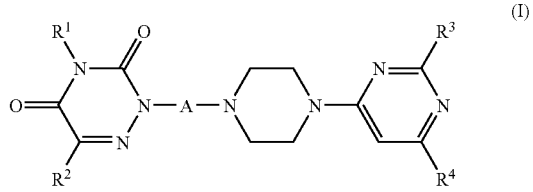

(I)

wherein

A is a saturated or unsaturated hydrocarbon chain having a chain length of 4 to 6 carbon atoms, the hydrocarbon chain being unsubstituted or substituted by 1, 2 or 3 methyl groups;

$R^1$ is selected from the group consisting of hydrogen, $C_1$-$C_3$ alkyl and fluorinated $C_1$-$C_3$ alkyl;

$R^2$ is hydrogen, halogen, cyano, $C_1$-$C_3$ alkyl, $C_1$-$C_3$ alkoxy, fluorinated $C_1$-$C_3$ alkyl or fluorinated $C_1$-$C_3$ alkoxy;

$R^3$ is selected from the group consisting of branched $C_4$-$C_6$ alkyl and $C_3$-$C_6$ cycloalkyl; and $R^4$ is $C_1$-$C_6$ alkyl, $C_3$-$C_6$ cycloalkyl, fluorinated $C_1$-$C_3$-alkyl or fluorinated $C_3$-$C_6$ cycloalkyl;

or a physiologically tolerated salt, tautomer, or N-oxide thereof.

2. The compound as claimed in claim 1, wherein $R^1$ is hydrogen.

3. The compound as claimed in claim 1, wherein $R^2$ is selected from the group consisting hydrogen, methyl, ethyl, fluorinated $C_1$-alkyl, fluorine or chlorine.

4. The compound as claimed in claim 1, wherein $R^2$ is hydrogen.

5. The compound as claimed in claim 1, wherein $R^2$ is methyl.

6. The compound as claimed in claim 1, wherein A is selected from the group consisting of $(CH_2)_4$, $CH_2$—$CH_2$—$CH(CH_3)$—$CH_2$, $CH_2$—$CH(CH_3)$—$CH_2$—$CH_2$, cis $CH_2$—$CH$=$CH$—$CH_2$, trans $CH_2$—$CH$=$CH$—$CH_2$, cis $CH_2$—$CH$=$C(CH_3)$—$CH_2$, trans $CH_2$—$CH$=$C(CH_3)$—$CH_2$, cis $CH_2$—$C(CH_3)$=$CH$—$CH_2$ and trans $CH_2$—$C(CH_3)$=$CH$—$CH_2$.

7. The compound as claimed in claim 6, wherein A is $(CH_2)_4$.

8. The compound as claimed in claim 1, wherein $R^3$ is branched $C_4$-$C_6$-alkyl.

9. The compound as claimed in claim 8, wherein $R^3$ is tert-butyl.

10. The compound as claimed in claim 1, wherein $R^4$ is fluorinated $C_1$-$C_2$-alkyl, n-propyl, n-butyl, tert-butyl or cyclobutyl.

11. The compound as claimed in claim 10, wherein $R^4$ is trifluoromethyl.

12. The compound as claimed in claim 1, wherein A is $(CH_2)_4$, $R^1$ is hydrogen; $R^2$ is hydrogen or methyl; $R^3$ is branched $C_4$-$C_6$-alkyl; and $R^4$ is fluorinated $C_1$-$C_2$-alkyl, n-propyl, n-butyl, tert-butyl or cyclobutyl.

13. The compound as claimed in claim 12, wherein $R^2$ is hydrogen.

14. The compound as claimed in claim 12, wherein $R^3$ is tert-butyl.

15. The compound as claimed in claim 12, wherein $R^4$ is trifluoromethyl.

16. The compound according to claim 1, selected from the group consisting of:
2-{4-[4-(2-tert-Butyl-6-trifluoromethyl-pyrimidin-4-yl)-piperazin-1-yl]butyl}-2H-[1,2,4] triazine-3,5-dione;
2-{4-[4-(2-tert-Butyl-6-propyl-pyrimidin-4-yl)-piperazin-1-yl]butyl}-2H-[1,2,4] triazine-3,5-dione;
2-{4-[4-(2,6-Di-tert-butyl-pyrimidin-4-yl)-piperazin-1-yl]butyl}-2H-[1,2,4] triazine-3,5-dione;
2-{4-[4-(2-tert-Butyl-6-cyclobutyl-pyrimidin-4-yl)-piperazin-1-yl]butyl}-2H-[1,2,4] triazine-3,5-dione;
2-{4-[4-(2-tert-Butyl-6-trifluoromethyl-pyrimidin-4-yl)-piperazin-1-yl]butyl}-6-methyl-2H-[1,2,4] triazine-3,5-dione;
2-{4-[4-(2-tert-Butyl-6-propyl-pyrimidin-4-yl)-piperazin-1-yl]butyl}-6-methyl-2H-[1,2,4]triazine-3,5-dione; and
2-{4-[4-(2-tert-Butyl-6-trifluoromethyl-pyrimidin-4-yl)-piperazin-1-yl]butyl}-4-methyl-2H-[1,2,4] triazine-3,5-dione;
or a pharmacologically tolerated salt or tautomer thereof.

17. A pharmaceutical composition comprising at least one compound as claimed in claim 1, together with at least one physiologically acceptable carrier or auxiliary substance.

18. A method for treating schizophrenia comprising administering an effective amount of at least one compound as claimed in claim 1 to a subject in need thereof.

19. A method for treating a bipolar disorder comprising administering an effective amount of at least one compound as claimed in claim 1 to a subject in need thereof.

20. A method for treating drug addiction comprising administering an effective amount of at least one compound as claimed in claim 1 to a subject in need thereof.

* * * * *

UNITED STATES PATENT AND TRADEMARK OFFICE
CERTIFICATE OF CORRECTION

| | | |
|---|---|---|
| PATENT NO. | : 8,492,540 B2 | Page 1 of 1 |
| APPLICATION NO. | : 12/740714 | |
| DATED | : July 23, 2013 | |
| INVENTOR(S) | : Braje et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 237 days.

Signed and Sealed this
Twentieth Day of October, 2015

Michelle K. Lee
*Director of the United States Patent and Trademark Office*